(12) United States Patent
Rawson

(10) Patent No.: US 11,883,062 B2
(45) Date of Patent: Jan. 30, 2024

(54) MEDICAL DEVICE WITH GUIDEWIRE BRAKE

(71) Applicant: BOSTON SCIENTIFIC SCIMED, INC., Maple Grove, MN (US)

(72) Inventor: Robert Rawson, North Branch, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 169 days.

(21) Appl. No.: 17/135,982

(22) Filed: Dec. 28, 2020

(65) Prior Publication Data

US 2021/0236158 A1 Aug. 5, 2021

Related U.S. Application Data

(60) Provisional application No. 62/967,860, filed on Jan. 30, 2020.

(51) Int. Cl.
*A61B 17/3207* (2006.01)
*A61B 17/22* (2006.01)
*A61M 25/09* (2006.01)

(52) U.S. Cl.
CPC ............ *A61B 17/320758* (2013.01); *A61B 17/22031* (2013.01); *A61B 2017/22038* (2013.01);
(Continued)

(58) Field of Classification Search
CPC ...... A61B 17/320758; A61B 17/22031; A61B 2017/22038; A61B 2017/22094;
(Continued)

(56) References Cited

U.S. PATENT DOCUMENTS 5,779,722 A * 7/1998 Shturman ...... A61B 17/320758
606/159
9,220,529 B2 12/2015 Rivers et al.
(Continued)

FOREIGN PATENT DOCUMENTS

EP 2052756 A1 4/2009
EP 3040098 A2 7/2016
(Continued)

OTHER PUBLICATIONS

International Search Report and Written Opinion dated May 25, 2021 for International Application No. PCT/US2020/067233.

*Primary Examiner* — Shaun L David
*Assistant Examiner* — Rachael L Geiger
(74) *Attorney, Agent, or Firm* — Seager, Tufte & Wickhem, LLP

(57) ABSTRACT

Example medical devices are disclosed. An example medical device includes a handle having a distal end region, a proximal end region and an inner chamber. The medical device also includes a guidewire brake including an actuation member coupled to a first gripping member and a second gripping member. The first gripping member and a second gripping member are disposed within the inner chamber of the handle and at least a portion of the actuation member is positioned along an outer surface of the handle. Further, the first gripping member and the second gripping member are configured to shift between an unclamped configuration and a clamped configuration.

17 Claims, 6 Drawing Sheets

(52) U.S. Cl.
CPC .............. *A61B 2017/22094* (2013.01); *A61B 2017/320775* (2013.01); *A61M 2025/09116* (2013.01)

(58) Field of Classification Search
CPC ......... A61B 2017/320775; A61B 2017/22049; A61M 2025/09116; A61M 2025/09125; A61M 25/09
See application file for complete search history.

(56) References Cited

U.S. PATENT DOCUMENTS

| | | |
|---|---|---|
| 9,439,674 B2 | 9/2016 | Rydberg et al. |
| 2009/0124934 A1* | 5/2009 | Rabbitte ......... A61M 25/09041 600/585 |
| 2010/0211006 A1* | 8/2010 | Schmidt-Sorensen ...................... A61M 25/09041 604/95.01 |
| 2011/0077621 A1* | 3/2011 | Graham ............. A61M 39/1011 604/528 |
| 2014/0243734 A1* | 8/2014 | Eubanks ............ A61M 25/0113 604/95.01 |
| 2018/0304049 A1* | 10/2018 | Bennett ........... A61M 25/09041 |

FOREIGN PATENT DOCUMENTS

| | | |
|---|---|---|
| JP | 2015-512702 A | 4/2015 |
| JP | 2018-110745 A | 7/2018 |

* cited by examiner

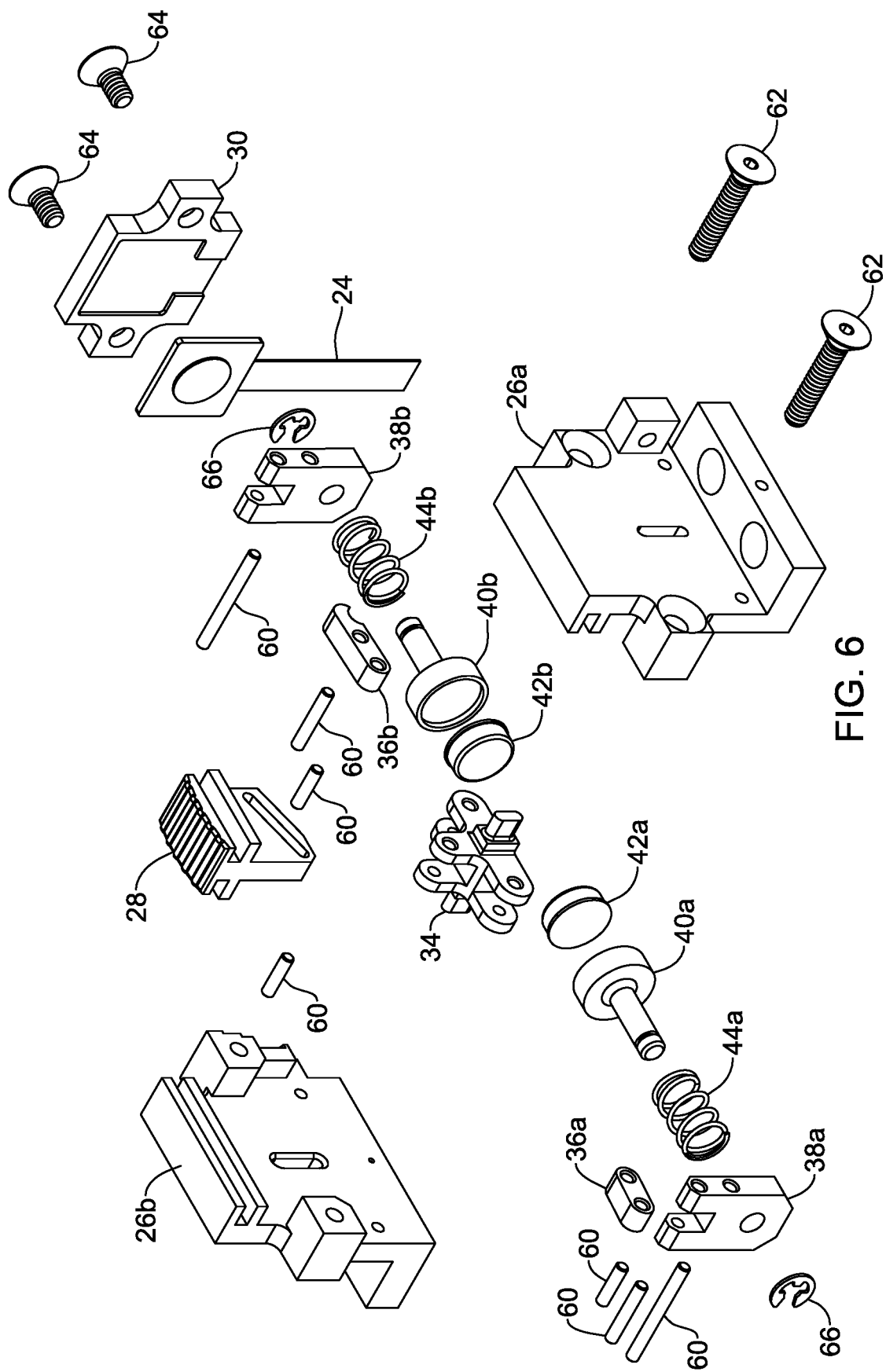

MEDICAL DEVICE WITH GUIDEWIRE BRAKE

CROSS-REFERENCE TO RELATED APPLICATIONS

This application claims the benefit of priority under 35 U.S.C. § 119 to U.S. Provisional Application Ser. No. 62/967,860, filed Jan. 30, 2020, the entirety of which is incorporated herein by reference.

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. In some cases a stent may be placed in the area of a treated occlusion. However, restenosis may occur in the stent, further occluding the vessel and restricting blood flow. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. A need remains for alternative atherectomy devices to facilitate crossing an occlusion.

BRIEF SUMMARY

This disclosure provides design, material, manufacturing method, and use alternatives for medical devices. An example medical device includes a handle having a distal end region, a proximal end region and an inner chamber. The medical device also includes a guidewire brake including an actuation member coupled to a first gripping member and a second gripping member. The first gripping member and a second gripping member are disposed within the inner chamber of the handle and at least a portion of the actuation member is positioned along an outer surface of the handle. Further, the first gripping member and the second gripping member are configured to shift between an unclamped configuration and a clamped configuration.

Alternatively or additionally to any of the embodiments above, wherein the first gripping member includes a first gripping pad and the second gripping member includes a second gripping pad, and wherein in the unclamped configuration at least a portion of the first gripping pad is spaced away from at least a portion of the second gripping pad and in the clamped configuration the first gripping pad contacts the second gripping pad.

Alternatively or additionally to any of the embodiments above, wherein in the clamped configuration the first gripping pad and the second gripping pad are configured to clamp a guidewire therebetween.

Alternatively or additionally to any of the embodiments above, wherein the first gripping pad and the second gripping pad are configured to exert a force on a guidewire such that the guidewire is prevented from shifting longitudinally, rotationally or both longitudinally and rotationally.

Alternatively or additionally to any of the embodiments above, wherein the actuation member is coupled to the first gripping member and the second gripping member via one or more linkages.

Alternatively or additionally to any of the embodiments above, wherein actuation of the actuation member shifts the guidewire brake between the unclamped configuration and the clamped configuration.

Alternatively or additionally to any of the embodiments above, wherein the actuation member is configured to be manually actuated.

Alternatively or additionally to any of the embodiments above, further comprising a sensor disposed along the guidewire brake.

Alternatively or additionally to any of the embodiments above, wherein the sensor is configured to sense if the guidewire brake is positioned in the clamped configuration.

Alternatively or additionally to any of the embodiments above, further comprising a control system disposed along the handle, and wherein the sensor is configured to send a signal to a control system indicating that the guidewire brake is positioned in the clamped configuration.

Alternatively or additionally to any of the embodiments above, further comprising a drive shaft coupled to the distal end region of the handle.

Alternatively or additionally to any of the embodiments above, further comprising an atherectomy burr coupled to the distal end of the drive shaft.

Another example atherectomy device includes a handle having a distal end region, a proximal end region and an inner chamber. The device also includes a drive shaft coupled to the distal end region of the handle, the drive shaft including an atherectomy burr disposed along a distal end of the drive shaft. The device also includes a guidewire brake including an actuation member coupled to a first gripping member and a second gripping member. The first gripping member and a second gripping member are disposed within the inner chamber of the handle and at least a portion of the actuation member is positioned along an outer surface of the handle. Further, the first gripping member and the second gripping member are configured to shift between an unclamped configuration and a clamped configuration.

Alternatively or additionally to any of the embodiments above, wherein the first gripping member includes a first gripping pad and the second gripping member includes a second gripping pad, and wherein in the unclamped configuration at least a portion of the first gripping pad is spaced away from at least a portion of the second gripping pad and in the clamped configuration the first gripping pad contacts the second gripping pad.

Alternatively or additionally to any of the embodiments above, wherein in the clamped configuration the first gripping pad and the second gripping pad are configured to clamp a guidewire therebetween.

Alternatively or additionally to any of the embodiments above, wherein the first gripping pad and the second gripping pad are configured to exert a force on a guidewire such that the guidewire is prevented from shifting longitudinally, rotationally or both longitudinally and rotationally.

Alternatively or additionally to any of the embodiments above, wherein the actuation member is coupled to the first gripping member and the second gripping member via one or more linkages.

Alternatively or additionally to any of the embodiments above, wherein actuation of the actuation member shifts the guidewire brake between the unclamped configuration and the clamped configuration.

Alternatively or additionally to any of the embodiments above, wherein the actuation member is configured to be manually actuated.

An example method of treating a tissue lesion includes advancing an atherectomy device over a guidewire to a lesion, the atherectomy device including a handle having a distal end region, a proximal end region and an inner chamber. The device also includes a drive shaft coupled to the distal end of the handle and an atherectomy burr coupled to the distal end of the drive shaft. The device also includes a guidewire brake including an actuation member coupled to a first gripping member and a second gripping member, wherein the first gripping member and a second gripping member are disposed within the inner chamber of the handle, and wherein at least a portion of the actuation member is positioned along an outer surface of the handle. The method also includes actuating the actuation member such that the first and second gripping members clamp the guidewire therebetween and rotating the atherectomy burr.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 6 is an exploded view of the guidewire brake shown in FIG. 3.

Figure 1:
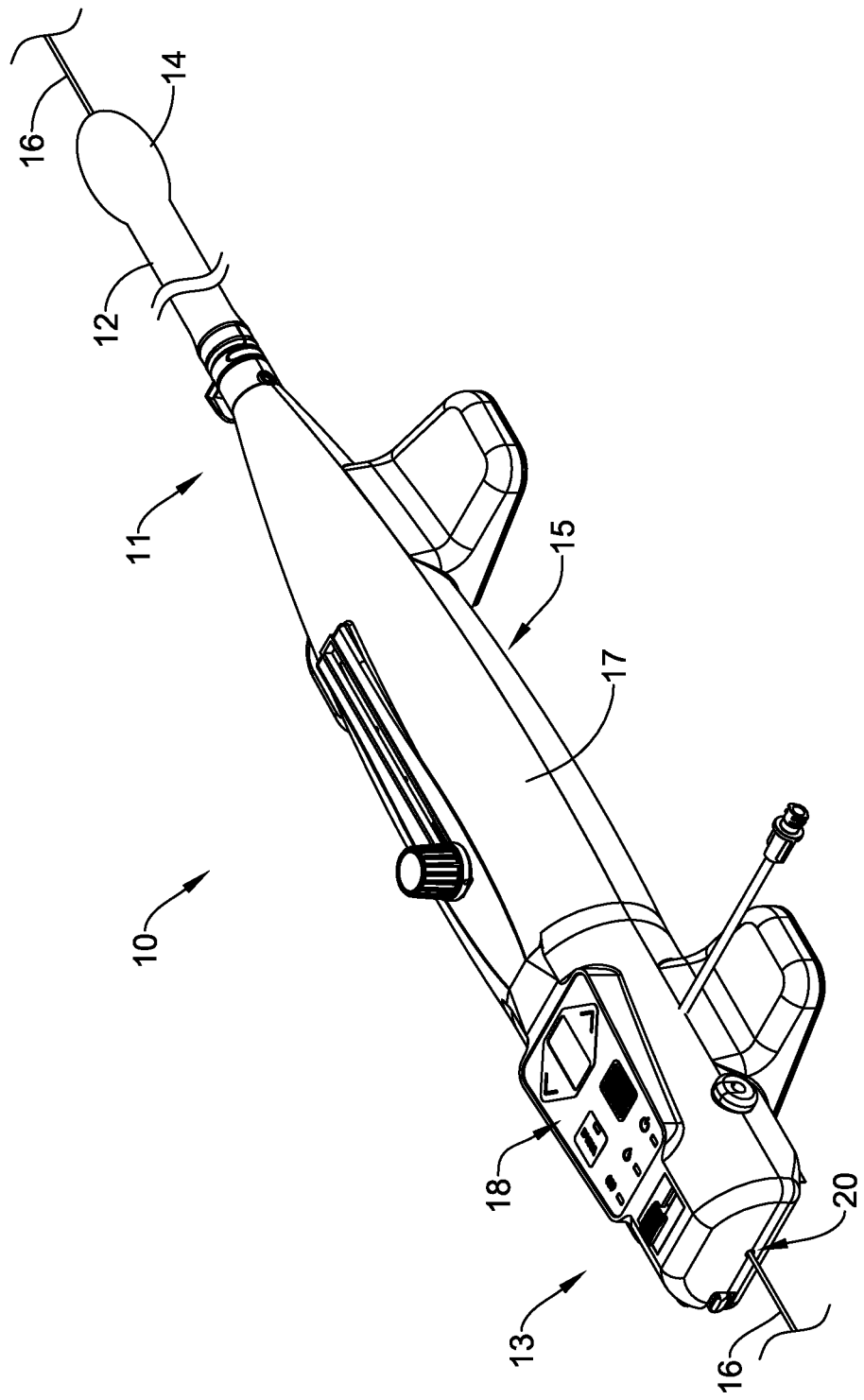
FIG. 1 is an example medical device.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

Many patients suffer from occluded arteries, other blood vessels, and/or occluded ducts or other body lumens which may restrict bodily fluid (e.g. blood, bile, etc.) flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. Ideally, the cutting element excises the occlusion without damaging the surrounding vessel wall and/or a previously implanted stent where restenosis has occurred. However, in some instances the cutting element may be manipulated and/or advanced such that it contacts the vessel wall and/or the stent. Therefore, it may be desirable to utilize materials and/or design an atherectomy device that can excise an occlusion without damaging the surrounding vessel and/or a previously implanted stent where restenosis has occurred. Additionally, it may be desirable to design a cutting element that may effectively remove hard occlusive material, such as calcified material, as well as softer occlusive material. The methods and systems disclosed herein may be designed to overcome at least some of the limitations of previous atherectomy devices while effectively excising occlusive material.

FIG. 1 illustrates an example medical device system 10. In some instances, the medical device system 10 may include an atherectomy system. For example, the atherectomy system 10 may include a handle member 15 having a distal end region 11 and a proximal end region 13. The distal end region of the handle 15 may be coupled to a drive shaft 12. Additionally, the system 10 may further include an end effector 14 coupled to the distal end of the drive shaft 12. In some instances, the end effector 14 may include an atherectomy burr.

Additionally, FIG. 1 illustrates that the medical device system 10 may include a housing 17. The housing 17 may include an inner chamber. In some examples, the medical device may also include a drive mechanism (not show in FIG. 1) disposed within the inner chamber of the housing 17. Further, it can be appreciated that the drive mechanism may be adapted to rotatably actuate the atherectomy burr 14 via rotation of the drive shaft 12. For example, it can be appreciated that the drive mechanism may be designed to rotate the drive shaft 12, thereby rotating the atherectomy burr 14 which is coupled to the distal end of the drive shaft 12.

Further, the atherectomy system 10 may include a control system (not shown in FIG. 1) which is adapted to regulate operation of the drive mechanism. In some cases, the atherectomy system 10 may include a user interface 18 that may be operably coupled to the control system such that the user interface 18 is able to display information regarding the performance of the drive mechanism. This information may, for example, include one or more of an instantaneous speed of the drive mechanism, an instantaneous torque being experienced by the atherectomy burr 14, and the like. In some instances, the atherectomy system 10 may not include the user interface 18. In some cases, the atherectomy burr 14 may also be referred to as being or including a cutting head or a cutting member, and these terms may be used interchangeably.

As illustrated in FIG. 1, in some instances the distal end of the atherectomy burr 14 may include an aperture (not shown in FIG. 1) that is configured to permit a guidewire 16 to extend through and internal cavity (e.g., lumen) of the atherectomy burr 14. Additionally, the guidewire 16 may be able to extend through a lumen of the drive shaft 12 and enter the internal chamber of the housing 17. Further, FIG. 1 illustrates that the guidewire may extend through the internal chamber of the housing 17 whereby it may exit the proximal end region 13 of the housing through an aperture 20 extending through a wall of the housing 17. In other words, the aperture 20 may span across the wall of the housing 17 (from a location outside the handle 15 to a location within the internal chamber of the housing 17).

A discussed above, a medical procedure utilizing atherectomy includes advancing a rotating cutting element (e.g., the atherectomy burr 14) through an occlusion to form or enlarge a pathway through the occlusion. It can be appreciated that, in some instances, the guidewire 16 may be positioned adjacent to the occlusion prior to the advancement of the atherectomy burr 14 through the occlusion. For example, prior to advancing a rotating atherectomy burr 14 through an occlusion, a clinician may manipulate the guidewire 16 such that it is positioned adjacent to the occlusion. In other instances, the clinician may manipulate the guidewire 16 such that it is positioned across the occlusion. However, after positioning the guidewire 16 (but prior to advancement of the rotating atherectomy burr 14 across the occlusion), it may be necessary for the clinician to "lock" (e.g., secure) the guidewire 16 such that it may not move (rotationally or longitudinally) relative to the handle 15. Preventing the guidewire 16 from moving (rotationally or longitudinally) relative to the handle 15 may be necessary because it may provide a more stable guidewire path along which the drive shaft 12 may be advanced. It may be necessary that the guidewire be locked to prevent rotation for patient safety. The rotating atherectomy burr which the guidewire passes through may rotate at speeds over 200,000 revolutions per minute. If the guidewire is not securely locked and rotates with the atherectomy burr, the guidewire may begin to "whip" and cause damage (e.g., punctures or tears) to a vein or artery within which it is spinning.

Figure 2:
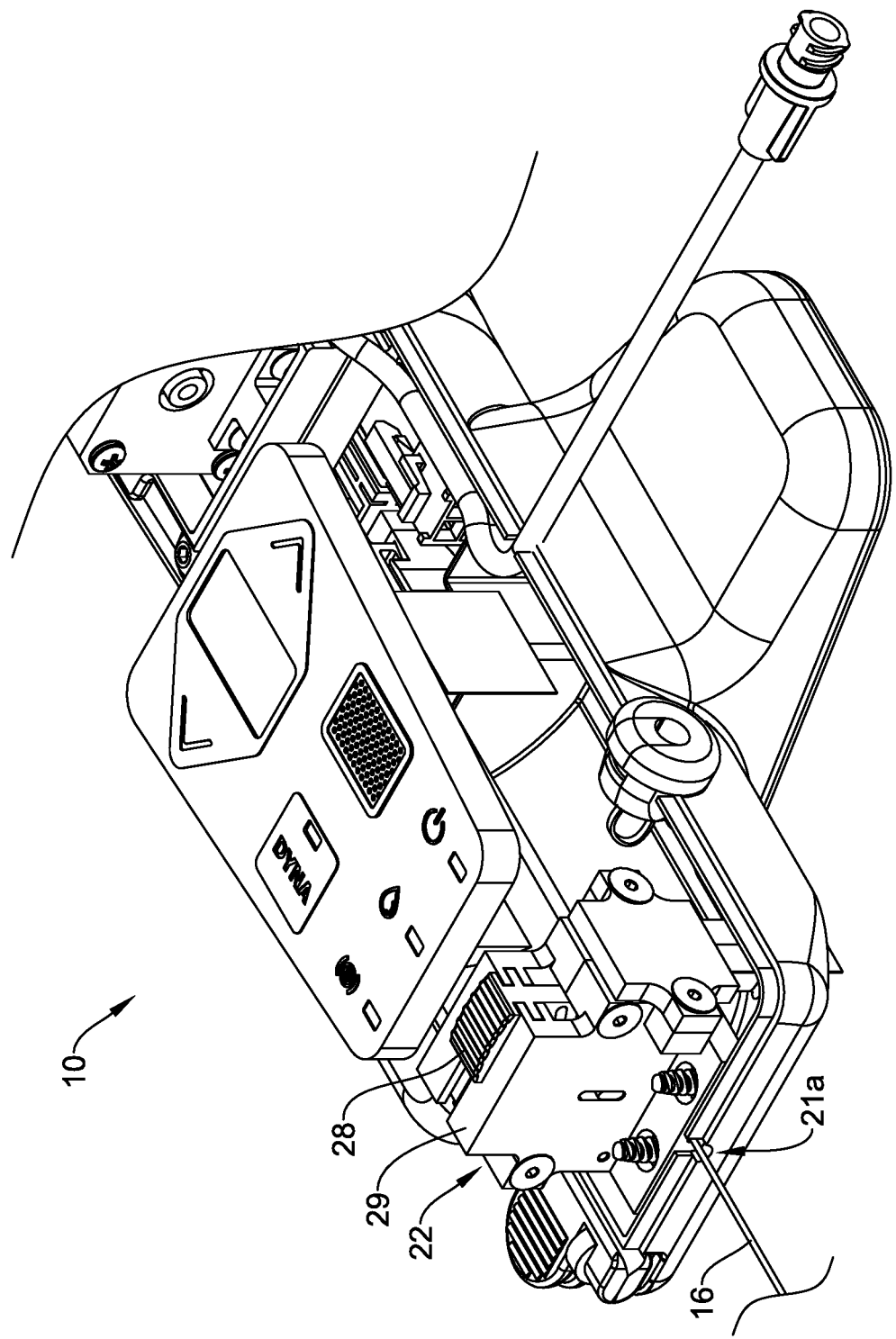
FIG. 2 illustrates a portion of the medical device shown in FIG. 1.

To that end, FIG. 2 illustrates the proximal end region 13 of the handle 15 (for clarity, FIG. 2 illustrates the handle 15 with the housing 17 having been removed, thereby exposing the internal components positioned along the proximal end region 13 of the handle 15). As shown in FIG. 2, one of the components positioned within the internal chamber of the housing 17 may include a guidewire brake 22 (it can be appreciated that in some cases, the guidewire brake 22 may be referred to as a guidewire lock or guidewire clamp). FIG. 2 further illustrates the guidewire 16 extending through an aperture 21a, located in guidewire brake 22. It can be appreciated that the aperture 21a may be aligned with the aperture 20, which was discussed above with respect to FIG. 1. As discussed above, the guidewire brake 22 may be disposed within an interior of the handle 15 (e.g., within the internal chamber of the handle 15) and may be configured to reversibly clamp down onto the guidewire 16 in order to prevent movement of the guidewire 16 during operation of the atherectomy system 10.

As will be discussed in greater detail below, the guidewire brake 22 may be designed to shift between an open (e.g., unclamped) configuration and a closed (e.g., clamped) configuration. Additionally, shifting the guidewire brake 22 between the clamped configuration (whereby the guidewire 16 is secure and prevented from moving rotationally and longitudinally) and the unclamped configuration (whereby the guidewire 16 is free to move rotationally and longitudinally) may be accomplished by sliding an actuation member 28 along a top surface 29 of the guidewire brake 22. In other words, the guidewire brake 22 may be designed to actuate (e.g., shift) between the unclamped configuration and the clamped configuration.

Additionally, it can be appreciated that, in some examples, shifting the guidewire brake 22 between the unclamped and the clamped configuration may include manually actuating the actuation member 28. In other words, a clinician operating the medical device 10 may manually (e.g., with his or her hand) shift (e.g., slide) the actuation member from left-to-right or vice versa. This manual actuation of the actuation member 28 may shift the guidewire brake 22 between the unclamped configuration and the clamped configuration. Designing the guidewire brake 22 to include a manual actuation member 28 may be desirable as it may permit the clinician to operate the brake independent of electrical power. In other words, the clinician may be able to apply or release the brake 22 independent of whether power is being supplied to the medical device 10. In the event a clinician has to remove the medical device 10 from a guidewire 16, the clinician will be able to release the guidewire brake 22 from the guidewire 16 via manual manipulation of the actuation member 28.

Figure 3:
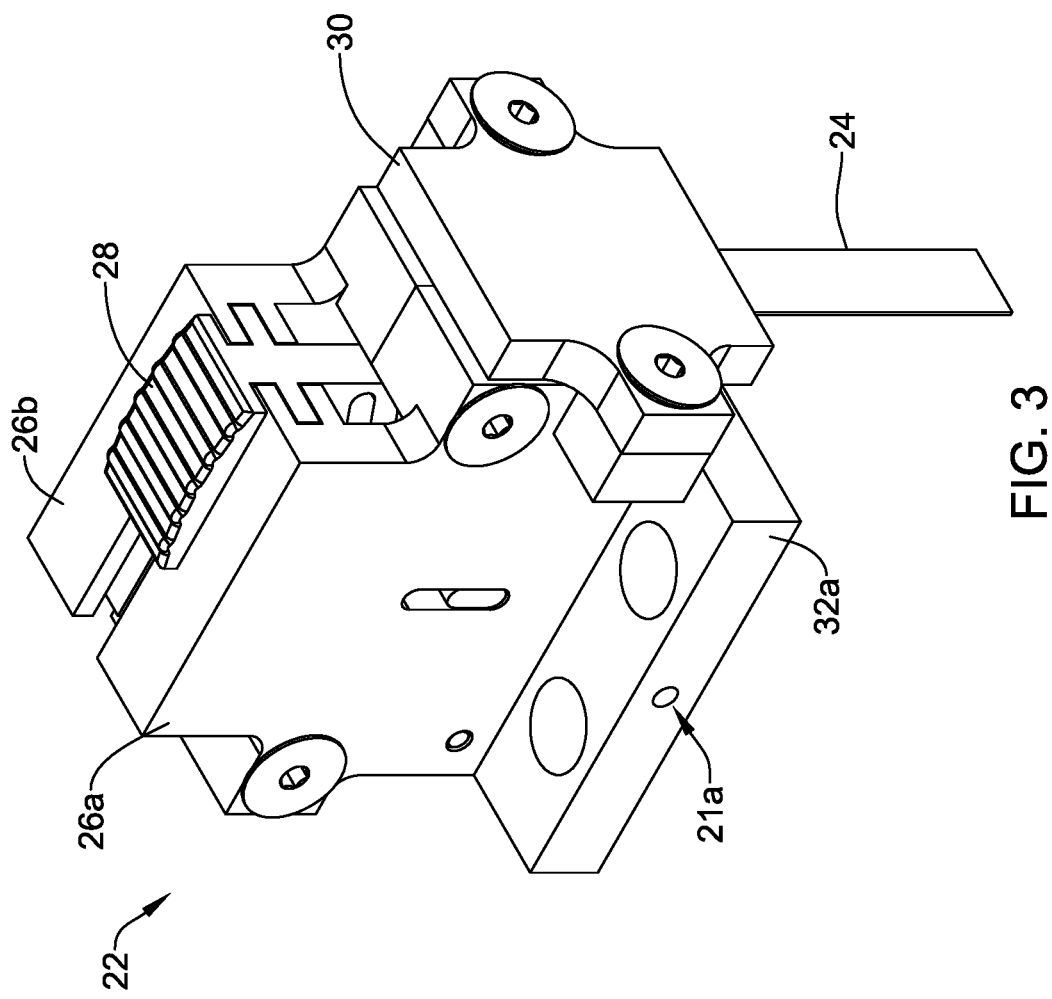
FIG. 3 illustrates a guidewire brake of the medical device shown in FIG. 1.

FIG. 3 illustrates the guidewire brake 22 discussed above. The guidewire brake 22 may include a first housing 26a coupled to a second housing 26b. In some instances, the first housing 26a may be coupled to the second housing 26b via a clamshell configuration. Securement of the first housing 26a to the second housing 26b may be accomplished via one or more pins, screws, bolts, etc.

As discussed above, the guidewire brake 22 may further include an actuation member 28 disposed between the first housing 26a and the second housing 26b. The actuation member 28 may be designed to shift (e.g., slide, traverse, actuate, etc.) within a track formed between the first housing member 26a and the second housing member 26b. As may be appreciated from FIG. 1, the actuation member 28 may extend outside of the housing 17 of the handle member 15. Positioning the actuation member 28 outside of the housing may permit a clinician to manually shift the actuation member 28 between the clamped configuration and the unclamped configuration, as described above.

As described above, FIG. 3 illustrates the aperture 21a extending within the first housing member 26a. In particular, FIG. 3 illustrates the aperture 21a extending through a base portion 32a of the first housing member 26a. The base portion 32a may be designed such that when the base portion 32a is positioned within the internal chamber of the handle 15, the aperture 21a may be aligned with the aperture 20 extending through the housing 17.

FIG. 3 further illustrates that, in some examples, the guidewire brake 22 may include a sensor 24. The sensor 24 may be coupled to the guidewire brake 22 via a sensor housing 30. In other words, a portion of the sensor 24 may be located within the sensor housing 30, whereby the sensor housing 30 is coupled to the first housing member 26a and the second housing member 26b. The sensor 24 may include a variety of different sensor configurations. For example, sensor 24 may include contact sensors, pressure sensors, force sensors, optical sensors, or any other type of suitable sensor.

It can further be appreciated that the sensor 24 may be designed to communicate with the control system located in the handle 15. In some examples, the sensor 24 may be able to sense the status of the guidewire brake 22 and send a signal to the control system indicating whether the guidewire brake 22 is in a clamped configuration or an unclamped configuration. It can be further appreciated that the user interface 18 may provide a visual display of the status of the guidewire brake 22

Figure 4:
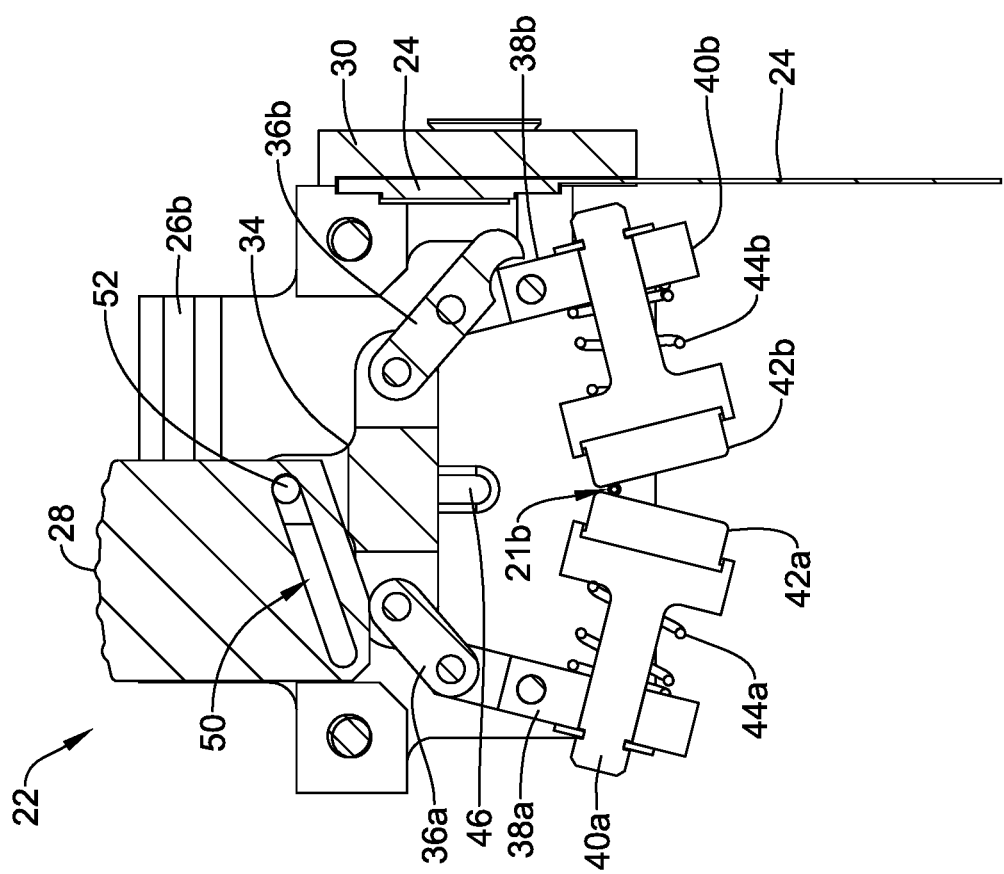
FIG. 4 illustrates a portion of the guidewire brake shown in FIG. 3.

FIG. 4 illustrates a front view of the guidewire brake 22 whereby the first housing member 26a has been removed to expose interior components of the guidewire brake 22. It can be appreciated that FIG. 4 illustrates the guidewire brake 22 in an unclamped configuration. For example, FIG. 4 shows the actuation member 28 slide to a leftmost position relative to the second housing member 26b. In this position, a first gripping member 40a (including a first gripping pad 42a disposed on its distal end region of the first gripping member 40a) may be spaced away from a second gripping member 40b (including a second gripping pad 42b disposed on the distal end region of the second gripping member), thereby creating a space between at least a portion of the first gripping pad 42a and at least a portion of the second gripping pad 42b which may permit the guidewire 16 to move freely between the first gripping pad 42a and the second gripping pad 42b. As discussed above, FIG. 4 further illustrates a portion of the sensor 24 positioned between the second housing member 26b and the sensor housing 30.

Additionally, it can be appreciated from FIG. 4 that the guidewire 16 may extend through an aperture 21b located within the second housing member 26b. Additionally, the aperture 21b may be aligned with the aperture 21a (located in the first housing member 26a) and the aperture 20 extending through the housing 17 (as describe above). The aperture 21b may be positioned such that it vertically aligns the guidewire 16 within a vertical plane of the first gripping pad 42a and the second gripping pad 42b. For example, it can be appreciated that the guidewire 16 may extend through the internal cavity of the housing 17, through the aperture 21b, between the first gripping pad 42a and the second gripping pad 42b, and through both the aperture 21a and the aperture 20. As discussed above, the apertures 21b, 21a and 20 may be designed such that they position the guidewire 16 within a vertical plane between the first gripping member 42a and second gripping member 42b.

FIG. 4 further illustrates that the actuation member 28 may be coupled to the first gripping pad 42a and the second gripping pad 42b through a series of linkages. For example, FIG. 4 illustrates that the actuation member 28 may be coupled to a central link 34. As shown in FIG. 4, the actuation member 28 may include a slit 50 which may be configured to accept a pin 52 extending therethrough. The pin 52 may be coupled to the central link 34. As shown in FIG. 4, because the slit 50 is positioned at an angle relative to the horizontal axis of the central link 34, left-to-right actuation (e.g., sliding) of the actuation member 28 may force the central link 34 downward. Additionally, the central link 34 may be restricted to vertical motion as the pin 52 may also extend into a vertical channel 46 formed in the second housing member 26b. Therefore, left-to-right actuation (e.g., sliding) of the actuation member 28 may force the central link 34 vertically downward.

To that end, the central link 34 may be coupled to a first gripping member 40a and a second gripping member 40b via a series of linkages 36a/36b/38a/38b. It can be appreciated that the distal end region of each of the first gripping member 40a and the second gripping member 40b may be coupled to the first gripping pad 42a and the second gripping pad 42b, respectively. Further, each of the first gripping member 40a and the second gripping member 40b may be held in tension via a first spring 44a and a second spring 44b. It can be appreciated that when in a clamped configuration, the first spring 44a and a second spring 44b provide an outward force which translates to a compressive force being placed on the guidewire 16 via the first gripping pad 42a and the second gripping pad 42b.

Figure 5:
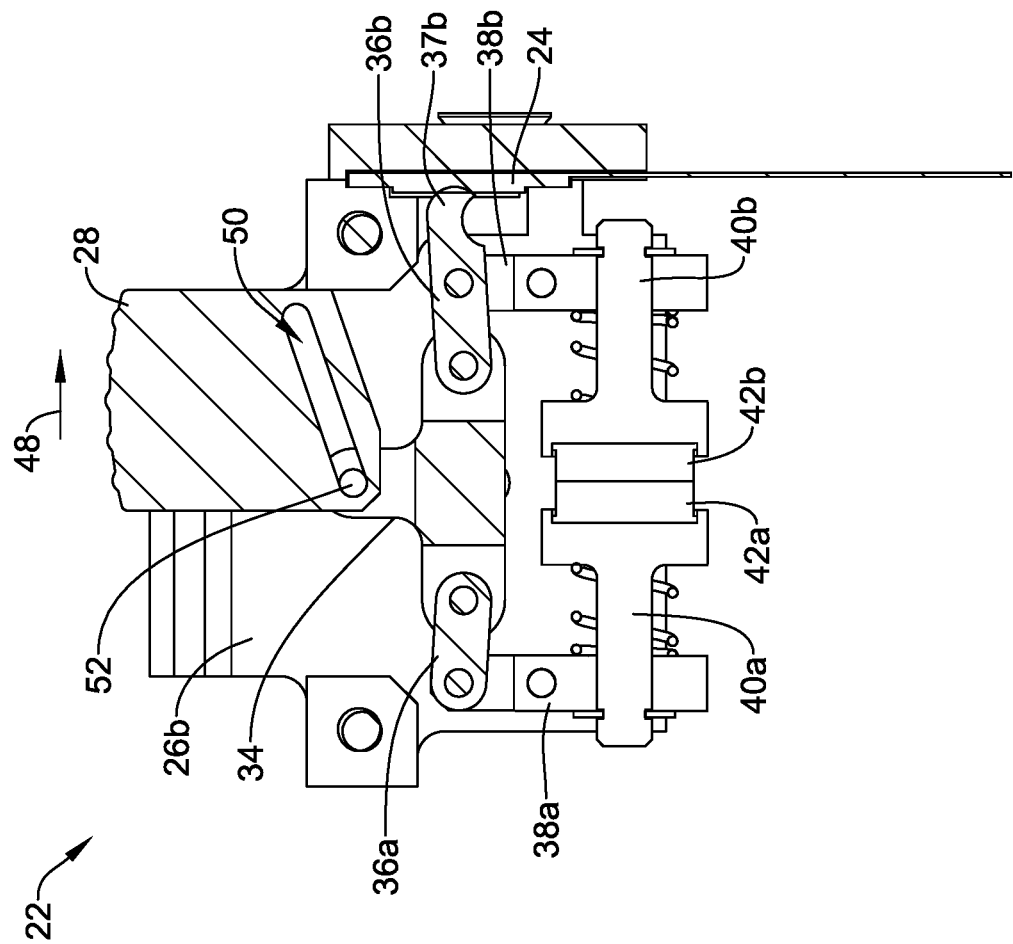
FIG. 5 illustrates a portion of the guidewire brake shown in FIG. 3.

FIG. 5 illustrates the guidewire brake 22 after the actuation member 28 has been shifted (e.g., slid) in a left-to-right direction (as depicted by the arrow 48) relative to the second housing member 26b. It should be noted that the actuation member 28 is being shifted in a left-to-right direction when viewed from the proximal end of the guidewire brake 22 (e.g., when viewed from the proximal end as the guidewire brake 22 is positioned within the handle 15).

It can be appreciated that sliding the actuation member 28 in a left-to-right direction forces the central linkage 34 vertically downward (as described above), thereby causing the first gripping pad 42a to move toward the second gripping pad 42b via the series of linkages 36a/36b/38a/38b coupled to both the first gripping member 40a and the second gripping member 40b. It is noted that even though the guidewire 16 is not shown in FIG. 5, it can be appreciated that FIG. 5 illustrates the clamped configuration of the guidewire brake 22, whereby the guidewire 16 would be positioned between the first gripping pad 42a and the second gripping pad 42b.

It can be further appreciated that FIG. 5 illustrates that in the second configuration, the distal end 37b of the linkage 36b may contact the sensor 24. This point-to-point contact between the distal end 37b of the linkage 36b and the sensor 24 may be sensed by the sensor 24. After the sensor 24 senses the contact it may send a signal to the control system of the medical device 10. The signal may indicate that the guidewire brake 22 is positioned in a clamped configuration. Further, this information may be displayed on the user interface 18 (shown in FIG. 1).

FIG. 6 illustrates an exploded view of the guidewire brake 22 described above. For example, FIG. 6 illustrates the first housing member 26a, the second housing member 26b, the actuation member 28, the central linkage 34, the sensor 24, the sensor housing 30, the first gripping member 40a, the second gripping member 40b, the first spring 44a, the second spring 44b, the first gripping pad 42a, second gripping pad 42b and the connecting linkages 36a/36b/38a/36b. Further, it can be appreciated that aforementioned components may be connected with one another via multiple pins 60, clips 66 and first bolts 62 and second bolts 64.

The materials that can be used for the medical device 10 or components of the medical device 10 disclosed herein may include those commonly associated with medical devices. For simplicity purposes, the following discussion makes reference to medical device 10 or components of the medical device 10. However, this is not intended to limit the devices and methods described herein, as the discussion may be applied to other similar devices disclosed herein.

Medical device 10 or components of the medical device 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of medical device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10 or the components of the medical device 10 to achieve the same result.

In some embodiments, a degree of Magnetic Resonance Imaging (MRI) compatibility is imparted into the medical device 10 or components of the medical device 10. For example, medical device 10, or portions thereof, may be made of a material that does not substantially distort the image and create substantial artifacts (e.g., gaps in the image). Certain ferromagnetic materials, for example, may not be suitable because they may create artifacts in an MM image. Medical device 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device, comprising:
   a handle having a distal end region, a proximal end region and an inner chamber;
   a guidewire brake including an actuation member coupled to a first gripping member and a second gripping member; and
   a sensor attached to the guidewire brake;
   wherein the first gripping member and the second gripping member are disposed within the inner chamber of the handle;
   wherein at least a portion of the actuation member is positioned along an outer surface of the handle;

wherein the first gripping member is coupled to the actuation member by a first pivotal linkage and the second gripping member is coupled to the actuation member via a second pivotal linkage different from the first pivotal linkage;

wherein the first gripping member and the second gripping member are configured to shift between an unclamped configuration and a clamped configuration.

2. The medical device of claim 1, wherein the first gripping member includes a first gripping pad and the second gripping member includes a second gripping pad, and wherein in the unclamped configuration at least a portion of the first gripping pad is spaced away from at least a portion of the second gripping pad and in the clamped configuration the first gripping pad contacts the second gripping pad.

3. The medical device of claim 2, wherein in the clamped configuration the first gripping pad and the second gripping pad are configured to clamp a guidewire therebetween.

4. The medical device of claim 3, wherein the first gripping pad and the second gripping pad are configured to exert a force on a guidewire such that the guidewire is prevented from shifting longitudinally, rotationally or both longitudinally and rotationally.

5. The medical device of claim 2, wherein actuation of the actuation member shifts the guidewire brake between the unclamped configuration and the clamped configuration.

6. The medical device of claim 5, wherein the actuation member is configured to be manually actuated.

7. The medical device of claim 1, wherein the sensor is configured to sense if the guidewire brake is positioned in the clamped configuration.

8. The medical device of claim 7, further comprising a control system disposed along the handle, and wherein the sensor is configured to send a signal to the control system indicating that the guidewire brake is positioned in the clamped configuration.

9. The medical device of claim 1, further comprising a drive shaft coupled to the distal end region of the handle.

10. The medical device of claim 9, further comprising an atherectomy burr coupled to the distal end of the drive shaft.

11. An atherectomy device, comprising:
a handle having a distal end region, a proximal end region and an inner chamber;
a drive shaft coupled to the distal end region of the handle, the drive shaft including an atherectomy burr disposed along a distal end of the drive shaft; and
a guidewire brake including an actuation member coupled to a first gripping member and a second gripping member; and
a sensor attached to the guidewire brake;
wherein the first gripping member and the second gripping member are disposed within the inner chamber of the handle;
wherein the first gripping member is coupled to the actuation member by a first pivotal linkage and the second gripping member is coupled to the actuation member via a second pivotal linkage different from the first pivotal linkage;
wherein at least a portion of the actuation member is positioned along an outer surface of the handle;
wherein the first gripping member and the second gripping member are configured to shift between an unclamped configuration and a clamped configuration.

12. The medical device of claim 11, wherein the first gripping member includes a first gripping pad and the second gripping member includes a second gripping pad, and wherein in the unclamped configuration at least a portion of the first gripping pad is spaced away from at least a portion of the second gripping pad and in the clamped configuration the first gripping pad contacts the second gripping pad.

13. The medical device of claim 12, wherein in the clamped configuration the first gripping pad and the second gripping pad are configured to clamp a guidewire therebetween.

14. The medical device of claim 13, wherein the first gripping pad and the second gripping pad are configured to exert a force on a guidewire such that the guidewire is prevented from shifting longitudinally, rotationally or both longitudinally and rotationally.

15. The medical device of claim 12, wherein actuation of the actuation member shifts the guidewire brake between the unclamped configuration and the clamped configuration.

16. The medical device of claim 15, wherein the actuation member is configured to be manually actuated.

17. A method of treating a tissue lesion, the method comprising:
advancing an atherectomy device over a guidewire to a lesion, the atherectomy device including:
a handle having a distal end region, a proximal end region and an inner chamber;
a drive shaft coupled to the distal end of the handle;
an atherectomy burr coupled to the distal end of the drive shaft;
a guidewire brake including an actuation member coupled to a first gripping member and a second gripping member, wherein the first gripping member and the second gripping member are disposed within the inner chamber of the handle, wherein the first gripping member is coupled to the actuation member by a first pivotal linkage and the second gripping member is coupled to the actuation member via a second pivotal linkage different from the first pivotal linkage, and wherein at least a portion of the actuation member is positioned along an outer surface of the handle; and
a sensor attached to the guidewire brake;
actuating the actuation member such that the first and second gripping members clamp the guidewire therebetween; and
rotating the atherectomy burr.

* * * * *